United States Patent
Do et al.

(10) Patent No.: US 11,322,259 B2
(45) Date of Patent: May 3, 2022

(54) PATIENT RISK STRATIFICATION BASED ON BODY COMPOSITION DERIVED FROM COMPUTED TOMOGRAPHY IMAGES USING MACHINE LEARNING

(71) Applicant: THE GENERAL HOSPITAL CORPORATION, Boston, MA (US)

(72) Inventors: Synho Do, Lexington, MA (US); Florian Fintelmann, Boston, MA (US); Hyunkwang Lee, Boston, MA (US)

(73) Assignee: The General Hospital Corporation, Boston, MA (US)

(\*) Notice: Subject to any disclaimer, the term of this patent is extended or adjusted under 35 U.S.C. 154(b) by 0 days.

(21) Appl. No.: 16/644,890

(22) PCT Filed: Sep. 10, 2018

(86) PCT No.: PCT/US2018/050176
§ 371 (c)(1),
(2) Date: Mar. 5, 2020

(87) PCT Pub. No.: WO2019/051358
PCT Pub. Date: Mar. 14, 2019

(65) Prior Publication Data
US 2020/0211710 A1    Jul. 2, 2020

Related U.S. Application Data (60) Provisional application No. 62/555,771, filed on Sep. 8, 2017.

(51) Int. Cl.
*G16H 50/30* (2018.01)
*A61B 34/10* (2016.01)
(Continued)

(52) U.S. Cl.
CPC ............ *G16H 50/30* (2018.01); *A61B 6/032* (2013.01); *A61B 6/5217* (2013.01);
(Continued)

(58) Field of Classification Search
CPC ............ G06T 7/11; G06T 2207/10081; G06T 2207/20084; G06T 2207/30008;
(Continued)

(56) References Cited

U.S. PATENT DOCUMENTS
2010/0088264 A1    4/2010   Teverofskiy

OTHER PUBLICATIONS

Andrearczyk V, et al. Using filter banks in Convolutional Neural Networks for texture classification. Pattern Recognit Lett. 84: 63-69. doi:10.1016/j.patrec.2016.08.016, 2016.
(Continued)

*Primary Examiner* — Manuchehr Rahmjoo
(74) *Attorney, Agent, or Firm* — Quarles & Brady LLP (57) ABSTRACT

A system and method for determining patient risk stratification is provided based on body composition derived from computed tomography images using segmentation with machine learning. The system may enable real-time segmentation for facilitating clinical application of body morphological analysis sets. A fully-automated deep learning system may be used for the segmentation of skeletal muscle cross sectional area (CSA). Whole-body volumetric analysis may also be performed. The fully-automated deep segmentation model may be derived from an extended implementation of a Fully Convolutional Network with weight initialization of a pre-trained model, followed by post processing to eliminate intramuscular fat for a more accurate analysis.

20 Claims, 6 Drawing Sheets

(51) Int. Cl.
    G06T 7/11      (2017.01)
    G06T 7/155     (2017.01)
    G16H 15/00     (2018.01)
    G16H 30/40     (2018.01)
    A61B 6/03      (2006.01)
    A61B 6/00      (2006.01)
    G06T 7/00      (2017.01)

(52) U.S. Cl.
    CPC ............ *A61B 6/5223* (2013.01); *A61B 34/10* (2016.02); *G06T 7/0016* (2013.01); *G06T 7/11* (2017.01); *G06T 7/155* (2017.01); *G16H 15/00* (2018.01); *G16H 30/40* (2018.01); *A61B 2034/107* (2016.02); *G06T 2207/10081* (2013.01); *G06T 2207/20084* (2013.01); *G06T 2207/30008* (2013.01); *G06T 2207/30016* (2013.01); *G06T 2207/30041* (2013.01); *G06T 2207/30048* (2013.01); *G06T 2207/30061* (2013.01); *G06T 2207/30096* (2013.01)

(58) Field of Classification Search
    CPC . G06T 2207/30016; G06T 2207/30041; G06T 2207/30048; G06T 2207/30061; G06T 2207/30096; G06T 7/0016; G06T 7/155; G16H 15/00; G16H 50/30; G16H 30/40; A61B 2034/107; A61B 34/10; A61B 6/032; A61B 6/5217; A61B 6/5223; G06N 3/0454; G06N 3/08
    See application file for complete search history.

(56) References Cited

OTHER PUBLICATIONS

Anthimopoulos M, et al. Lung Pattern Classification for Interstitial Lung Diseases Using a Deep Convolutional Neural Network. IEEE Trans Med Imaging. doi:10.1109/TML.2016.2535865, 2016.

Blauwhoff-Buskermolen S, et al. Loss of Muscle Mass During Chemotherapy Is Predictive for Poor Survival of Patients With Metastatic Colorectal Cancer. J Clin Oncol. 34:1339-1344. doi:10.1200/JCO.2015.63.6043, 2016.

Boutin Rd, et al. Sarcopenia: Current Concepts and Imaging Implications. AJR Am J Roentgenol. 205: W255-66. doi:10.2214/AJR.15.14635, 2015.

Chung H, et al. Automated segmentation of muscle and adipose tissue on CT images for human body composition analysis. SPIE Medical Imaging. International Society for Optics and Photonics; p. 72610K-72610K-8. doi:10.1117/12.812412, 2009.

Cimpoi, M, et al. "Deep filter banks for texture recognition and segmentation." Proceedings of the IEEE conference on computer vision and pattern recognition. 2015.

Dodge S, et al. Understanding how image quality affects deep neural networks. 2016 Eighth International Conference on Quality of Multimedia Experience (QoMEX). IEEE; pp. 1-6. doi:10.1109/QoMEX.2016.7498955.

Englesbe MJ, et al. Sarcopenia and mortality after liver transplantation. J Am Coll Surg. 211:271-278. doi:10.1016/j.jamcollsurg.2010.03.039, 2010.

Gao Y, et al. Accurate Segmentation of CT Male Pelvic Organs via Regression—Based Deformable Models and Multi-Task Random Forests. IEEE Trans Med Imaging. 35: 1532-1543. doi:10.1109/TMI.2016.2519264, 2016.

Greenspan H, et al. Guest Editorial Deep Learning in Medical Imaging: Overview and Future Promise of an Exciting New Technique. IEEE Trans Med Imaging. 35: 1153-1159. 2016. doi:10.1109/TMI.2016.2553401.

Havaei M, et al. Brain tumor segmentation with Deep Neural Networks. Med Image Anal. 35: 18-31. doi:10.1016/j.media.2016.05.004, Jan. 2017.

International Searching Authority, International Search Report and Written Opinion for application PCT/US2018/050176. dated Dec. 12, 2018.

Kamiya N, et al. Automated recognition of the psoas major muscles on Xray CT images. Conf Proc IEEE Eng Med Biol Soc. 2009: 3557-3560. doi:10.1109/IEMBS.2009.5332597, 2009.

Kamiya N, et al. Automated segmentation of psoas major muscle in X-ray CT images by use of a shape model: preliminary study. Radiol Phys Technol. 5: 5-14. doi:10.1007/s12194-011-0127-0, 2012.

Kamiya N, et al. Automated segmentation of recuts abdominismuscle using shape model in X-ray CT images. Conf Proc IEEE Eng Med Biol Soc. 2011: 7993-7996. doi:10.1109/IEMBS.2011.6091971, 2011.

Kuroki LM, et al. Pre-operative assessment of muscle mass to predict surgical complications and prognosis in patients with endometrial cancer. Ann Surg Oncol. 22: 972-979. doi:10.1245/s10434-014-4040-8, 2015.

Lee H, et al. Fully Automated Deep Learning System for Bone Age Assessment. J Digit Imaging, doi:10.1007/s10278-017-9955-8, Aug. 2017.

Lee, H, et al. "Pixel-level deep segmentation: artificial intelligence quantifies muscle on computed tomography for body morphometric analysis." Journal of digital imaging 30.4 (Jun. 26, 2017): 487-498.

Liskowski P, et al. Segmenting Retinal Blood Vessels with Deep Neural Networks. IEEE Trans Med Imaging.: 1-1. doi:10.1109/tmi.2016.2546227, 2016.

Long J, et al. Fully convolutional networks for semantic segmentation. Proceedings of the IEEE Conference on Computer Vision and Pattern Recognition, pp. 3431-3440. 2015.

Martin L, et al. Cancer cachexia in the age of obesity: skeletal muscle depletion is a powerful prognostic factor, independent of body mass index. J Clin Oncol. 31:1539-1547. doi:10.1200/JCO.2012.45.2722, 2013.

McDonald AM, et al. CT Measures of Bone Mineral Density and Muscle Mass Can Be Used to Predict Noncancer Death in Men with Prostate Cancer. Radiology. 282: 475-483. doi:10.1148/radiol.2016160626, Feb. 2017.

Mitsiopoulos N, et al. Cadaver validation of skeletal muscle measurement by magnetic resonance imaging and computerized tomography. J Appl Physiol. 85:115-122. Available: https://www.ncbi.nlm.nih.gov/pubmed/9655763, 1998.

Moeskops P, et al. Automatic segmentation of MR brain images with a convolutional neural network. IEEE Trans Med Imaging. doi:10.1109/TMI.2016.2548501, 2016.

Moisey LL, et al. Skeletal muscle predicts ventilator-free days, ICU-free days, and mortality in elderly ICU patients. Crit Care. 17: R206. doi:10.1186/cc12901, 2013.

Pecorelli N, et al. Effect of sarcopenia and visceral obesity on mortality and pancreatic fistula following pancreatic cancer surgery. Br J Surg. 103: 434-442. doi:10.1002/bjs.10063, 2016.

Pereira S, et al. Brain Tumor Segmentation using Convolutional Neural Networks in MRI Images. IEEE Trans Med Imaging. doi:10.1109/TMI.2016.2538465, 2016.

Polan DF, et al. Tissue segmentation of computed tomography images using a Random Forest algorithm: a feasibility study. Phys Med Biol. 61: 6553-6569. doi:10.1088/0031-9155/61/17/6553, 2016.

Popuri K, et al. Body Composition Assessment in Axial CT Images Using FEM-Based Automatic Segmentation of Skeletal Muscle. IEEE Trans Med Imaging. 35: 512-520. doi:10.1109/TMI.2015.2479252, 2016.

Popuri K, et al. FEM-based automatic segmentation of muscle and fat tissues from thoracic CT images. 2013 IEEE 10th International Symposium on Biomedical Imaging, pp. 149-152. doi:10.1109/ISBI.2013.6556434, 2013.

Prado CMM, et al. Prevalence and clinical implications of sarcopenic obesity in patients with solid tumours of the respiratory and gastrointestinal tracts: a population-based study. Lancet Oncol. 9: 629-635. doi:10.1016/S1470-2045 (08)70153-0, 2008.

Reisinger KW, et al. Functional compromise reflected by sarcopenia, frailty, and nutritional depletion predicts adverse postoperative outcome after colorectal cancer surgery. Ann Surg. 261: 345-352. doi:10.1097/SLA.0000000000000628, 2015.

(56) References Cited

OTHER PUBLICATIONS

Roth HR, et al. DeepOrgan: Multi-level Deep Convolutional Networks for Automated Pancreas Segmentation. Medical Image Computing and Computer-Assisted Intervention—MICCAI 2015. Springer, Cham; pp. 556-564. doi:10.1007/978-3-319-24553-9_68, 2015.
Segev OL, et al. Image quality in obese patients undergoing 256-row computed tomography coronary angiography. Int J Cardiovasc Imaging. 28: 633-639. doi:10.1007/s10554-011-9848-8, 2012.
Shen W, et al. Total body skeletal muscle and adipose tissue volumes: estimation from a single abdominal cross-sectional image. J Appl Physiol. 97: 2333-2338. doi:10.1152/japplphysiol.00744.2004, 2004.
Shuster A, et al. The clinical importance of visceral adiposity: a critical review of methods for visceral adipose tissue analysis. Br J Radiol. 85: 1-10. doi:10.1259/bjr/38447238, 2012.
Weijs PJM, et al. Low skeletal muscle area is a risk factor for mortality in mechanically ventilated critically ill patients. Crit Care. 18: R12. doi:10.1186/cc13189, 2014.
Zhao B, et al. Automated quantification of body fat distribution on volumetric computed tomography. J Comput Assist Tomogr. 30: 777-783. doi:10.1097/01.rct.0000228164.08968.e8, 2006.

PATIENT RISK STRATIFICATION BASED ON BODY COMPOSITION DERIVED FROM COMPUTED TOMOGRAPHY IMAGES USING MACHINE LEARNING

CROSS-REFERENCE TO RELATED APPLICATIONS

This application represents the national stage entry of PCT International Application No. PCT/US2018/050176 filed Sep. 10, 2018, which claims the benefit of U.S. Provisional Patent Application Ser. No. 62/555,771, filed on Sep. 8, 2017, and entitled "Patient risk stratification based on body composition derived from computed tomography images using machine learning" incorporated herein by reference in their entirety.

STATEMENT REGARDING FEDERALLY SPONSORED RESEARCH

N/A

BACKGROUND

Deep learning has demonstrated enormous success in improving diagnostic accuracy, speed of image interpretation, and clinical efficiency for a wide range of medical tasks, ranging from the interstitial pattern detection on chest CT to bone age classification on hand radiographs. Particularly, a data-driven approach with deep neural networks has been actively utilized for several medical image segmentation applications, ranging from segmenting brain tumors on magnetic resonance images, organs of interest on CT to segmenting the vascular network of the human eye on fundus photography. This success is attributed to its capability to learn representative and hierarchical image features from data, rather than relying on manually engineered features based on knowledge from domain experts.

Image segmentation, also known as pixel-level classification, is the process of partitioning all pixels in an image into a finite number of semantically non-overlapping segments. In medical imaging, image segmentation has been considered a fundamental process for various medical applications including disease diagnosis, prognosis, and treatments. In particular, muscle segmentation on computed tomography (CT) for body composition analysis has emerged as a clinically useful risk stratification tool in oncology, radiation oncology, intensive care and surgery. Cadaver studies have established muscle cross sectional area (CSA) at the level of the third lumbar vertebral (L3) body as a surrogate marker for lean body muscle mass. These studies applied semi-automated threshold-based segmentation with pre-defined Hounsfield Unit (HU) ranges to separate lean muscle mass from fat. However, segmentation errors require manual correction based on visual analysis by highly-skilled radiologists. As a result, semi-automated body composition analysis on large datasets is impractical due to the expense and time required. Thus, there is a role for automated tissue segmentation in order to bring body composition analysis into clinical practice.

Adipose tissue segmentation on CT images may be performed as fat can be thresholded with a consistent HU range (−190 to −30). Muscle segmentation is less straightforward as muscle and neighboring organs have overlapping HU values (−29 to 150). Few published strategies exist for automated muscle segmentation with various approaches. One series of publications focused on segmentation of a single muscle (psoas major). Another has studied segmentation involving a deformable shape model based on the ideal muscle appearance with fitting based on a statistical deformation model (SDM). Another study attempted to segment a 3D body CT data set with 7 segmentation classes including fat and muscle by classifying each class using random forest classifiers when given 16 image features extracted from statistical information and filter responses. All these attempts require sophisticated hand-crafted features to define knowledge-based parameters and select constraints for well-formed statistical shape and appearance models. As a result, these approaches cannot be generalized.

Pretreatment risk stratification is key for personalized medicine. While many physicians rely on an "eyeball test" to assess whether patients will tolerate major surgery or chemotherapy, "eyeballing" is inherently subjective and difficult to quantify. The concept of morphometric age derived from cross-sectional imaging has been found to correlate well with outcomes such as length of stay, morbidity, and mortality. However, the determination of morphometric age is time intensive and requires highly trained experts.

SUMMARY OF THE DISCLOSURE

The present disclosure addresses the aforementioned drawbacks by providing a system and method for determining patient risk stratification based on body composition derived from computed tomography images using machine learning. The system may enable real-time segmentation of muscle and fat tissue, for example, facilitating clinical application of body morphological analysis sets. In one configuration, a fully-automated deep learning system for the segmentation of skeletal muscle cross sectional area (CSA) is proposed. In an example configuration, the system may use an axial computed tomography (CT) image taken at the third lumbar vertebra (L3) for the CSA. A fully-automated deep segmentation model may be derived from an extended implementation of a Fully Convolutional Network with weight initialization of a pre-trained model, such as an ImageNet model, followed by post processing to eliminate intramuscular fat for a more accurate analysis.

In one configuration, a method for generating a report of a risk stratification for a subject using medical imaging is provided. The method includes acquiring an image of a region of interest of the subject and segmenting the image using a deep segmentation artificial intelligence network to generate a segmented image that distinguishes between at least two different materials in the image at a pixel-level. A morphological age may be calculated for the subject using the segmented image and a report of risk stratification may be generated for the subject at least based upon the calculated morphological age.

In some configurations, the artificial intelligence network may be a fully convolutional neural network adapted to segment the image at a pixel-level. The method may include measuring at least one of a Dice Similarity Coefficient (DSC) or a cross sectional area (CSA) error between a ground truth and a predicted segmentation of the image and selecting the artificial intelligence network from a plurality of networks based on a minimizing of the DSC or CSA. The plurality of networks may include different layered FCNs including at least an FCN of 32 layers, an FCN of 16 layers, an FCN of 8 layers, an FCN of 4 layers, and an FCN of 2 layers. The image may be a computed tomography (CT) image. The image may be converted to a grayscale image by converting from Hounsfield Units (HU) of the image using a grayscale. Converting may include setting grayscale values below a selected window width to zero and setting grayscale values above a window width to a maximum (2BIT−1), where BIT represents the available number of bits per pixel, and where grayscale values within the window width are determined using a slope (2BIT−1/window width).

In some configurations, the method includes calculating a morphological age of the subject by quantifying a cross sectional area of the segmented image. A report of risk stratification of the subject may be generated by determining at least one of a preoperative risk, a prediction of death, a tolerance to major surgery or chemotherapy, morbidity, mortality, or an expected length of hospital stay. The artificial intelligence network may also be trained with at least one labelled image and the segmenting may be performed in real-time.

In one configuration, a system is provided for generating a report of a risk stratification for a subject from medical images. The system includes a computer system configured to: i) acquire a medical image of a region of interest of the subject; ii) generate a segmented image by segmenting the image using a pixel-level deep artificial intelligence network to distinguish between at least two different materials in the image; iii) calculate a morphological age of the subject using the segmented image; and iv) generating a report of risk stratification of the subject based upon the calculated morphological age.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Muscle cross sectional area has been shown to correlate with a wide-range of posttreatment outcomes. However, integration of muscle CSA measurements in clinical practice have been limited by the time required to generate this data. By dropping calculation time from 1800 seconds to less than one second, research into new applications for morphometric analysis may be drastically sped up. CT is an essential tool in the modern healthcare arena with approximately 82 million CT examinations performed in the US in 2016. In lung cancer in particular, the current clinical paradigm has been on lesion detection and disease staging with an eye toward treatment selection. However, accumulating evidence suggests that CT body composition data could provide objective biological markers to help lay the foundation for the future of personalized medicine. Aside from preoperative risk stratification for surgeons, morphometric data may be used to predict death in radiation oncology and medical oncology patients.

In one configuration, a system and method for determining patient risk stratification is provided based on body composition derived from computed tomography images using machine learning. The system may enable real-time segmentation of muscle and fat tissue, for example, facilitating clinical application of body morphological analysis sets. In one configuration, a fully-automated deep learning system for the segmentation of skeletal muscle cross sectional area (CSA) is proposed. In an example configuration, the system may use an axial computed tomography (CT) image taken at the third lumbar vertebra (L3) for the CSA. In another configuration, whole-body volumetric analysis may be performed. A fully-automated deep segmentation model may be derived from an extended implementation of a Fully Convolutional Network with weight initialization of a pre-trained model, followed by post processing to eliminate intramuscular fat for a more accurate analysis.

In some configurations, varying window level (WL), window width (WW), and bit resolutions may be performed with post processing in order to better understand the effects of the parameters on the model performance. An example model, fine-tuned on 250 training images and ground-truth labels, achieves 0.93±0.02 Dice Similarity Coefficient (DSC) and 3.68±2.29% difference between predicted and ground truth muscle CSA on 150 held-out test cases. The fully automated segmentation system can be embedded into the clinical environment to accelerate the quantification of muscle and expanded to volume analysis of 3D data sets.

In some configurations, muscle segmentation maps may be used for ground-truth labeling during training, testing, and verification. Muscle segmentation maps may be manually tuned and reformatted into acceptable input for convolutional neural networks (CNN). The axial images and their corresponding color-coded images showing segmentation between muscle, internal space, and background may serve as original input data and ground truth labels, respectively. The main challenge for muscle segmentation is accurate differentiation of muscle tissue from neighboring organs due to their overlapping HU ranges. A boundary between organs and muscle may be manually drawn, or an automated routine may be used, setting the inside region as additional segmentation class ("Inside") in an effort to train the neural network to learn distinguishing features of muscle for a precise segmentation from adjacent organs. In one configuration, color-coded label images may be used and assigned to predefined label indices, including 0 (black) for "Background", 1 (red) for "Muscle", and 2 (green) for "Inside", before passing through CNNs for training.

Figure 1A:
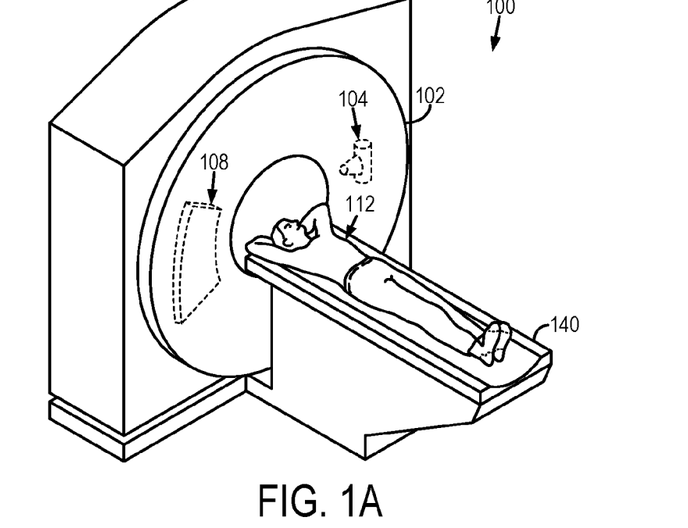
FIGS. 1A and 1B illustrate an example CT system that can be configured to operate one configuration of the present disclosure.
Figure 1B:
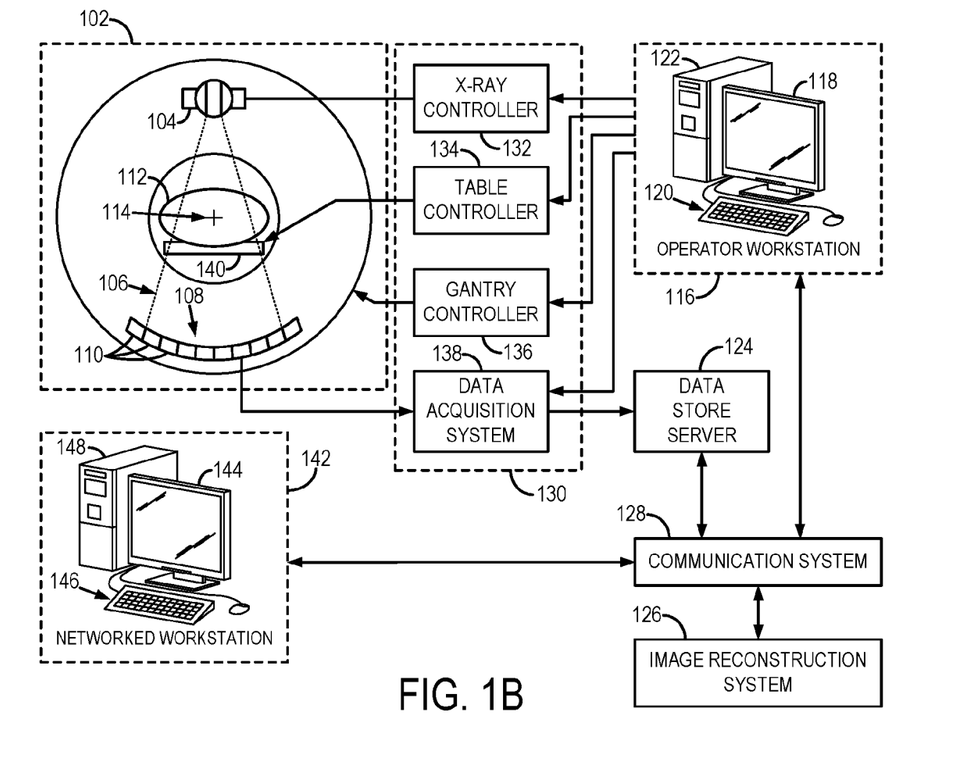

Referring particularly now to FIGS. 1A and 1B, an example of an x-ray computed tomography ("CT") imaging system 100 is illustrated. The CT system includes a gantry 102, to which at least one x-ray source 104 is coupled. The x-ray source 104 projects an x-ray beam 106, which may be a fan-beam or cone-beam of x-rays, towards a detector array 108 on the opposite side of the gantry 102. The detector array 108 includes a number of x-ray detector elements 110. Together, the x-ray detector elements 110 sense the projected x-rays 106 that pass through a subject 112, such as a medical patient or an object undergoing examination, that is positioned in the CT system 100. Each x-ray detector element 110 produces an electrical signal that may represent the intensity of an impinging x-ray beam and, hence, the attenuation of the beam as it passes through the subject 112. In some configurations, each x-ray detector 110 is capable of counting the number of x-ray photons that impinge upon the detector 110. In some configurations the system can include a second x-ray source and a second x-ray detector (not shown) operable at a different energy level than x-ray source 104 and detector 110. Any number of x-ray sources and corresponding x-ray detectors operable at different energies may be used, or a single x-ray source 104 may be operable to emit different energies that impinge upon detector 110. During a scan to acquire x-ray projection data, the gantry 102 and the components mounted thereon rotate about a center of rotation 114 located within the CT system 100.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. In general, the operator workstation 116 is in communication with a data store server 124 and an image reconstruction system 126. By way of example, the operator workstation 116, data store sever 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132, a table controller 134, a gantry controller 136, and a data acquisition system (DAS) 138. The x-ray controller 132 provides power and timing signals to the x-ray source 104 and the gantry controller 136 controls the rotational speed and position of the gantry 102. The table controller 134 controls a table 140 to position the subject 112 in the gantry 102 of the CT system 100.

The DAS 138 samples data from the detector elements 110 and converts the data to digital signals for subsequent processing. For instance, digitized x-ray data is communicated from the DAS 138 to the data store server 124. The image reconstruction system 126 then retrieves the x-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed images can then be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may be exchanged between the data store server 124, the image reconstruction system 126, and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
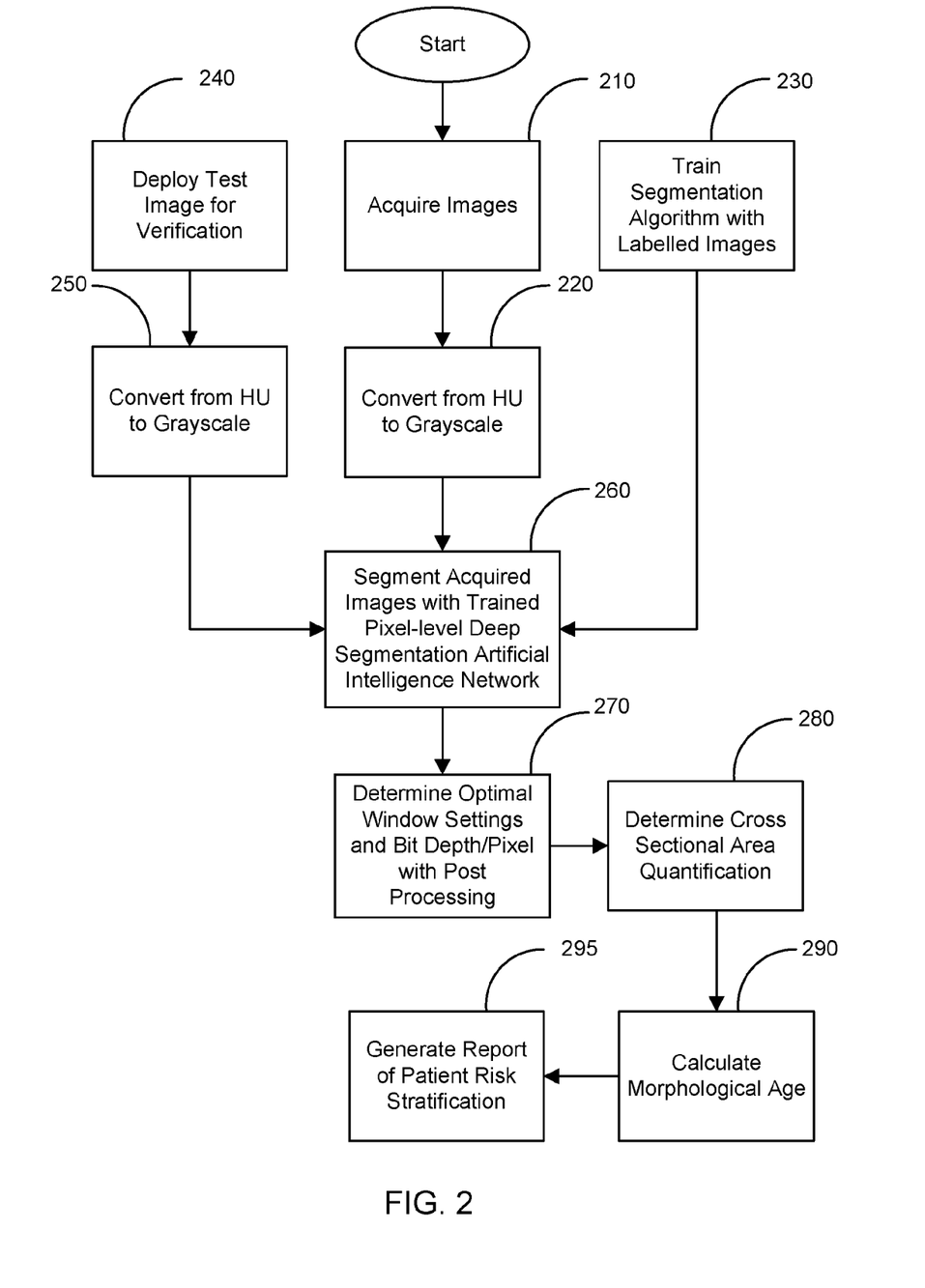
FIG. 2 is a flowchart depicting one configuration of the present disclosure, in which a pixel-level deep segmentation Artificial Intelligence network is deployed.

Referring to FIG. 2, a flowchart for one configuration of a fully-automated deep segmentation system for image segmentation is depicted. The process begins with images being acquired at step 210. Images may be acquired with a CT system as described in FIGS. 1A and 1B. The acquired images may be converted from Hounsfield Units (HU) to grayscale at step 220. Labelled images, where muscle and organs or "inside" pixels have been identified may be used to train the artificial intelligence segmentation network prior to processing the acquired images may be performed at step 230. A test image may be processed for verification or quality control purposes at 240, which may also be converted from HU to grayscale at 250. The test subset may be visually analyzed to identify any needed corrections. The trained pixel-level deep segmentation artificial intelligence network is used to segment the acquired images at step 260. An optimal combination of window settings and bit depth per pixel may be established with post processing to correct for any erroneous segmentation at step 270. "Optimal" may be based upon a desired level of maximizing image contrast or minimizing noise level, where the ability to distinguish between objects or between pixels that represent different material (such as muscle or organs) is optimized for a user. A cross sectional area quantification is determined at step 280 based upon the processed images. This cross sectional area quantification data is used to calculate a morphological age for a patient at step 290, which may be reported or displayed for a user with a risk stratification for the patient at step 295.

In one configuration, the segmentation model may be based on a fully convolutional network (FCN). Segmentation may be performed on muscle, organ tissue, background, adipose tissue, and the like. The advantages of an FCN are, first, that a set of convolutional structures enables learning highly representative and hierarchical abstractions from whole image input without excessive use of trainable parameters thanks to the usage of shared weights. Second, finetuning the trainable parameters of the FCN after weights are initialized with a pretrained model from a large-scale dataset allows the network to find the global optimum with a fast convergence of cost function when given a small training dataset. Third, the FCN may intentionally fuse different levels of layers by combining coarse semantic information and fine appearance information to maximize hierarchical features learned from earlier and later layers. However, a person of ordinary skill in the art will appreciate that other deep learning networks may be used, with several having been validated for natural image segmentation applications.

Error correction may be performed by subsequent FCN layers, such as to correct for incomplete muscle segmentation, incorrect organ segmentation and subcutaneous edema mischaracterized as muscle. Incomplete muscle segmentation may result from muscle being partly excluded from the appropriate region of the image. Incorrect organ segmentation may result from organs being partly included in the muscle region. Errors may be caused by overlapping HUs between muscle and adjacent organs and variable organ textural appearance. Edema may be mischaracterized when the radiographic appearance of edema, particularly in obese patients, has a similar HU range to muscle, leading to higher CSA than expected. Extensive edema tends to occur in critically ill patients, leading to potentially falsely elevated CSA in patients actually at higher risk for all interventions.

Figure 3:
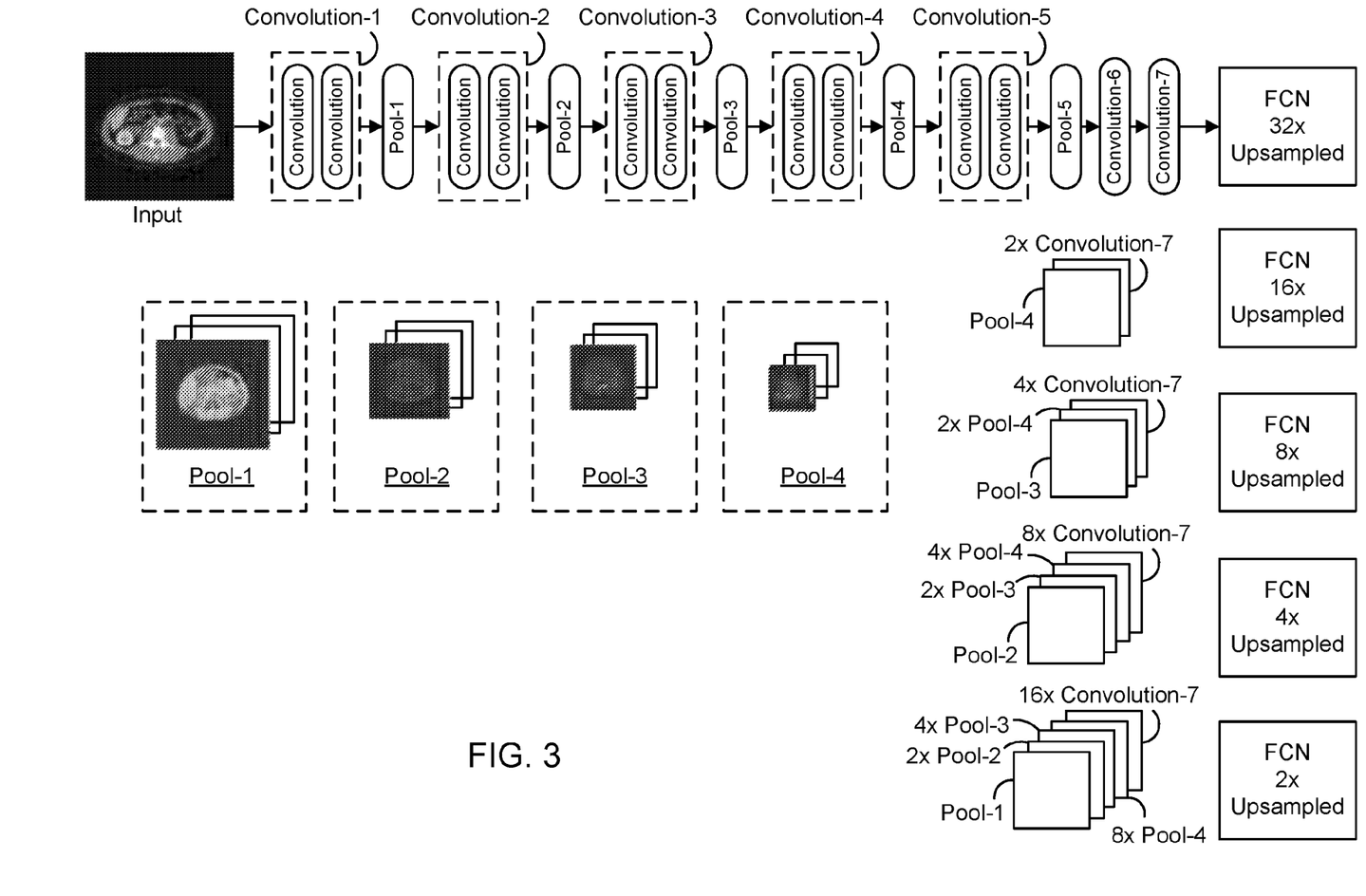
FIG. 3 is a schematic for one configuration of the artificial intelligence network in the form of a fully convolutional neural network that may feature different layers.

Referring to FIG. 3, FCN-32s, FCN-16s, FCN-8s fuse coarse-grained and fine-grained features and upsample them at stride 32, 16, and 8, for further precision. Prior implementations of FCN describe further fusion of earlier layers beyond pool3; however, this may only result in minor performance gains. Since muscle segmentation requires finer precision than stride 8, the process may be extended to FCN-4s and FCN-2s by fusing earlier layers further to meet the required detail and precision.

Figure 4:
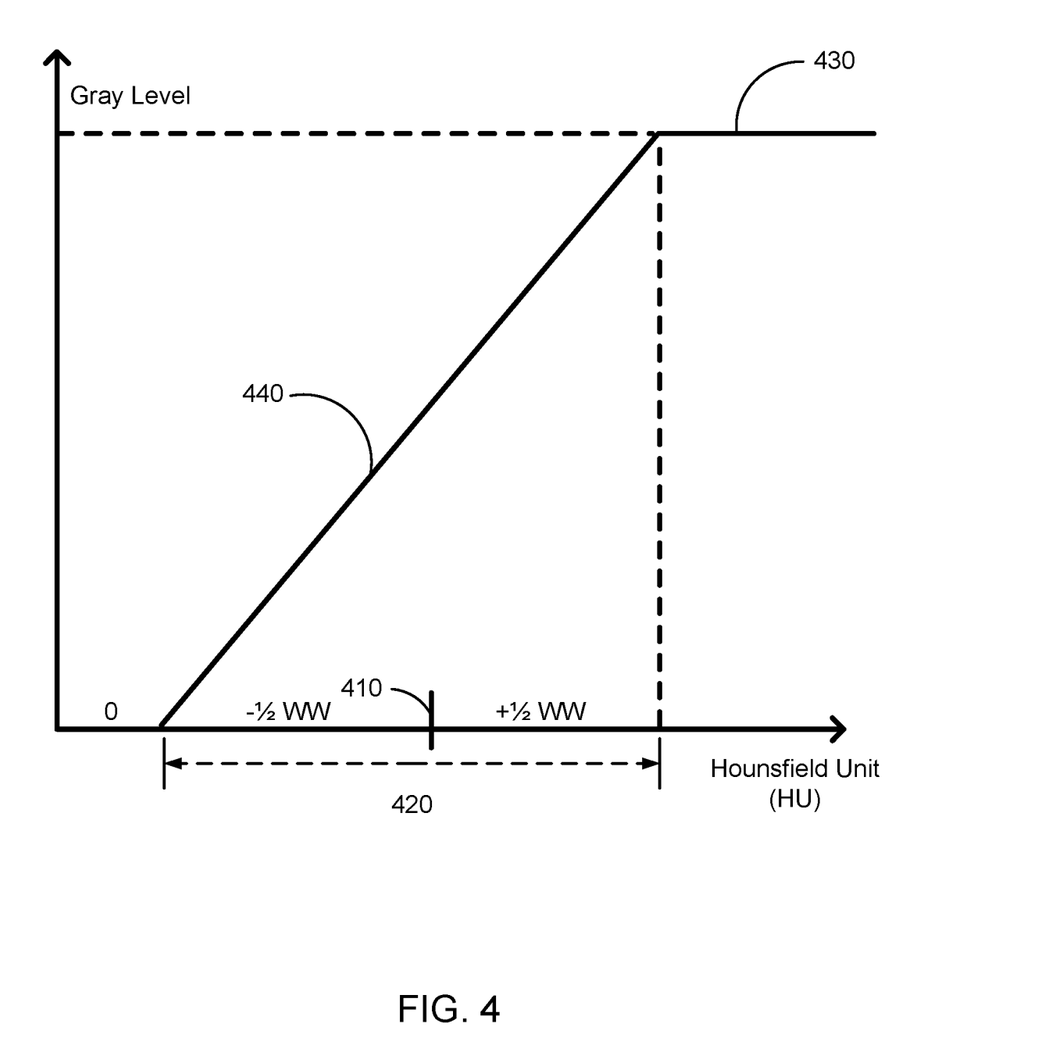
FIG. 4 is a graph of one configuration for converting between Hounsfield Units and grayscale.

Referring to FIG. 4, one configuration for converting from HU to grayscale is depicted. Medical images contain 12 to 16 bits per pixel, ranging from 4,096 to 65,536 shades of gray per pixel. A digital CT image has a dynamic range of 4,096 gray levels per pixel (12 bits per pixel), far beyond the limits of human perception; the human eye is only capable of differentiating roughly 32 shades of gray. Displays used for diagnostic CT interpretation support at most 8 bits per pixel, corresponding to 256 gray levels per pixel. To compensate for these inherent physiologic and technical limitations, images displayed on computer monitors can be adjusted by changing the window level (WL) 410 and window width (WW) 420, followed by assigning values outside the window range to minimum (0) or maximum ($2^{BIT}-1$) value 430. WL 410—the center of the window range—determines which HU values are converted into gray levels. WW determines how many of HU values are assigned to each gray level, related to the slope ($2^{BIT}-1/$WW) 440 of the linear transformation shown in FIG. 4. Bit depth per pixel, (BIT), is the available number of bits per pixel. BIT determines how many shades of gray are available per pixel. Optimal window setting configuration is dependent on the HUs of the region of interest (ROI) and the intrinsic image contrast and brightness. These settings are ultimately workarounds for the constraints of human perception. However, computer vision does not necessarily have these limitations.

CT images have been converted to grayscale previously with the commonly-used HU range for the target tissue or organ without studying the effect of window settings on the performance of their algorithms. While recent work has identified that image quality distortions limit the performance of neural networks in computer vision systems, the effect of window setting and bit resolution on image quality is often overlooked in medical imaging machine learning. In one configuration, the effects of window and BIT settings on segmentation performance are accounted for by sweeping different combinations of window configurations and bit depth per pixel.

In one configuration, a comparison measure is used that utilizes the Dice Similarity Coefficient (DSC) to compare the degree of overlap between the ground truth segmentation mask and the FCN-derived mask, calculated as Eq. 1.

$$DSC = \frac{2\times|\text{ground\_truth} \cap \text{predict}|}{|\text{ground\_truth}| + |\text{predict}|} \quad (1)$$

An additional comparison measure may be the cross sectional area (CSA) error, calculated as Eq. 2. This represents a standardized measure of the percentage difference in area between the ground-truth segmentation mask and the FCN-derived mask.

$$CSA\_error\_\% = \frac{|\text{ground\_truth} - \text{predict}|}{|\text{ground\_truth}|} \times 100 \quad (2)$$

Muscle tissue HUs do not overlap with adipose tissue HUs. As a result, a binary image of fat regions extracted using HU thresholding can be utilized to remove intramuscular fat incorrectly segmented as muscle.

In one configuration, the segmentation model may be trained by a stochastic gradient descent (SGD) routine with momentum. A minibatch size may be selected to optimize training efficiency. In one example, a minibatch size of 8 may be selected, with a fixed learning rate of 10-10, momentum 0.9, and a weight decay of 10-12. Training and validation losses may converge if the models are trained for a sufficient period of epochs, such as 500 epochs. The model may be selected to evaluate performance on a held-out test subset. The model may be trained using any appropriate system, such as a Devbox (NVIDIA Corp, Santa Clara, Calif.), which has four TITAN X GPUs with 12 GB of memory per GPU.

After training, segmentation may be performed using any appropriate hardware, such as a single TITAN X GPU. The time for performing segmentation may vary based upon the number of images and other parameters. For example, a segmentation took 25 seconds on average for 150 test images, corresponding to only 0.17 seconds per image. This represents a substantial time advantage over conventional segmentation routines. Accurate segmentation of muscle tissue by the semi-automated HU thresholding method requires roughly 20-30 minutes per slice on average. Other algorithms have been proposed that required between 1 to 3 minutes per slice. The ultra-fast deployment time of the present disclosure can allow for real-time segmentation in clinical practice. "Real-time" includes being able to process an image stack or set in a period of time, such as less than 1 minute or in less than 30 seconds or in less than 25 seconds, that allows for being able to display the segmentation results along with the original images for a user.

In some configurations, descriptive data may be presented as percentages for categorical variables and with standard deviation (SD) for continuous variables. In one example, a two-tailed statistical test with the alpha level set at 0.05 may be used. A Student's t-test for normally distributed values may also be used. Dichotomous variables may be compared using any appropriate test, such as the Mann Whitney U test, and ordinal variables may be compared using a test such as the Kruskal Wallis test. Inter-analyst agreement may be quantified with intraclass correlation coefficients (ICC). All statistical analyses may performed using any appropriate software package, such as the STATA software (version 13.0, StataCorp, College Station, Tex.).

The fully convolutional neural network may be adapted to suit the desired level of granularity, or the extent to which the original image is subdivided. To identify the best performing fully convolutional network, multiple models may be trained and evaluated. In one example, five models of increasing granularity—FCN-32s, FCN-16s, FCN-8s, FCN-4s, and FCN-2s—were trained and evaluated using a test dataset at (40,400) and 8 bits per pixel by measuring the Dice Similarity Coefficient (DSC) and CSA error between ground truth and predicted muscle segmentation. These results may be compared to the HU thresholding method, such as by selecting HU ranging from −29 to 150 to represent lean muscle CSA.

In one configuration, segmenting adipose tissue may be performed in a similar manner as described above, since fat can be thresholded within a unique HU range [−190 to −30]. Previously, an outer-muscle boundary to segment HU thresholded adipose tissue into Visceral Adipose Tissue (VAT) and Subcutaneous Adipose Tissue (SAT) has been used. However, precise boundary generation is dependent on accurate muscle segmentation. Using the current segmentation method with a subsequent adipose tissue thresholding system could quickly and accurately provide VAT and SAT values in addition to muscle CSA. Visceral adipose tissue has been implicated in cardiovascular outcomes and metabolic syndrome, and accurate fat segmentation would increase the utility of segmentation systems beyond cancer prognostication.

In an example study, 400 patients with an abdominal CT and lung cancer treated with either surgery or systemic therapy between 2007 and 2015 were identified in an institutional database. The surgical cohort (tumor stages I, II and III) represented a cross section of all patients who underwent lung cancer resection, while the medical cohort were patients who received chemotherapy (tumor stage IV). Only examinations with intravenous contrast were included to ensure consistency of HU values. 400 examinations of 200 females and 200 male patients were included in the study, as detailed in Table 1. A test subset of 150 cases was created for evaluating network performance. Patient characteristics of the entire cohort (n=400) and the test subset (n=150) are shown in Table 1. Note that there is no statistically significant difference between the entire cohort and the test subset.

TABLE 1

| Patient characteristics | n = 400 (entire cohort) | n = 150 (test subset) | p values |
|---|---|---|---|
| Age, mean (SD), years | 63 (12) | 62 (11) | 0.31 |
| Gender, no. (%) | | | 1 |
| Female | 200 (50) | 75 (50) | |
| Male | 200 (50) | 75 (50) | |
| Height, mean (SD), cm | 168 (10) | 168 (10) | 0.70 |
| Weight, mean (SD), kg | 77 (18) | 79 (19) | 0.16 |
| Lung cancer treatment, no. (%) | | | 0.78 |
| Systemic therapy | 227 (57) | 86 (57) | |
| Surgery | 173 (43) | 64 (43) | |
| Lung cancer stage, no. (%) | | | 0.84 |
| I | 102 (26) | 38 (25) | |
| II | 33 (8) | 10 (7) | |
| III | 38 (10) | 16 (11) | |
| IV | 227 (57) | 86 (57) | |

In the present example, images were acquired for routine clinical care with a tube current of approximately 360 mA, and a kV of approximately 120. Scanners were calibrated daily using manufacturer-supplied phantoms to ensure consistency in attenuation measurements in accordance with manufacturer specifications. Full resolution 512×512 pixel diagnostic quality CT examinations were loaded onto a research workstation running OsiriX without downsampling (Pixmeo, Bernex, Switzerland). Segmentation maps of skeletal muscle CSA at the level of L3 were created on a single axial image using semi-automated threshold-based segmentation (thresholds −29 to +150 HU). Analyzed muscles included the transversus abdominis, external and internal abdominal obliques, rectus abdominis, erector spinae, psoas major and minor and quadratus lumborum. A research assistant blinded to all other data created the segmentation maps, which were corrected as necessary by a fellowship-trained board-certified radiologist. A subset of the images were randomly selected and then re-analyzed by a second research assistant with an inter-analyst agreement of 0.998. These muscle segmentation maps were used for ground-truth labeling during training, testing, and verification.

Differences in body habitus could represent a confounding feature if the network were to be presented unbalanced examples, particularly because prior work has demonstrated that obese patients have higher image noise. To minimize this possibility, patients in the example study were categorized into eight groups based on gender and body mass index (BMI). We randomly selected 25 male and 25 female patients from the groups with normal weight, overweight, and obese in order to create a subset of 150 cases to be withheld for testing. All underweight cases were included in the training dataset without being used for testing due to their small number. The other 250 cases were used for training. We chose the best model out of several trained models by selecting the last model after the loss became converged for a sufficiently long period of training time, approximately 500 epochs. The best CNN was evaluated using the held-out test datasets to determine how much the predicted muscle regions overlap with the ground truth. In order to make a fair comparison, the same seed value was used for the random selection from the test dataset for each experiment.

In the current example study, to identify the best performing fully convolutional network, five models of increasing granularity—FCN-32s, FCN-16s, FCN-8s, FCN-4s, and FCN-2s—were trained and evaluated using the test dataset at (40,400) and 8 bits per pixel by measuring the Dice Similarity Coefficient (DSC) and CSA error between ground truth and predicted muscle segmentation. These results were compared to the HU thresholding method, selecting HU ranging from −29 to 150 to represent lean muscle CSA.

Subsequently, the performance of the best FCN model (FCN-2s) was compared with seven different combinations of window settings for each bit depth per pixel—(40,400), (40, 240), (40,800), (40,1200), (−40,400), (100,400), and (160,400) expressed in (WL,WW) and 8, 6, and 4 bit resolutions per pixel. The selected window ranges cover the HU range of lean tissue [−29 to 150] for a fair comparison to see if partial image information loss degrades model performance. These window settings contain extreme window ranges as well as typical ones. For example, the window setting (40,240) has a range of −80 to 160 HU values, which corresponds to almost the HU range of lean muscle, while the configuration (40,1200) converts all HU values between −560 and 1240 into shades of gray resulting in low image contrast.

Figure 5A:
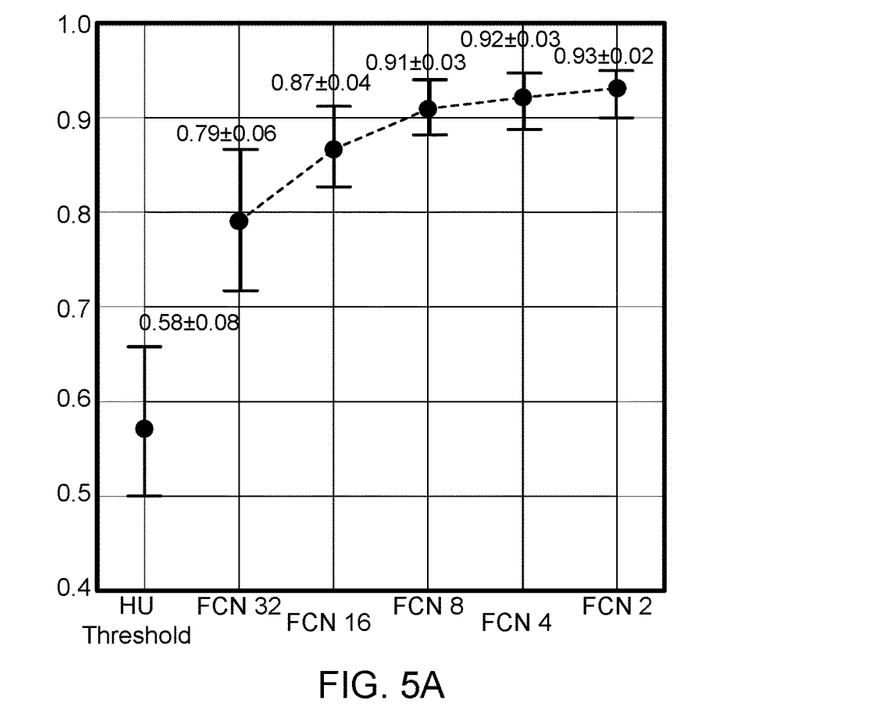
FIG. 5A is a graph of Dice Similarity Coefficient (DSC) from one example application of the present disclosure.
Figure 5B:
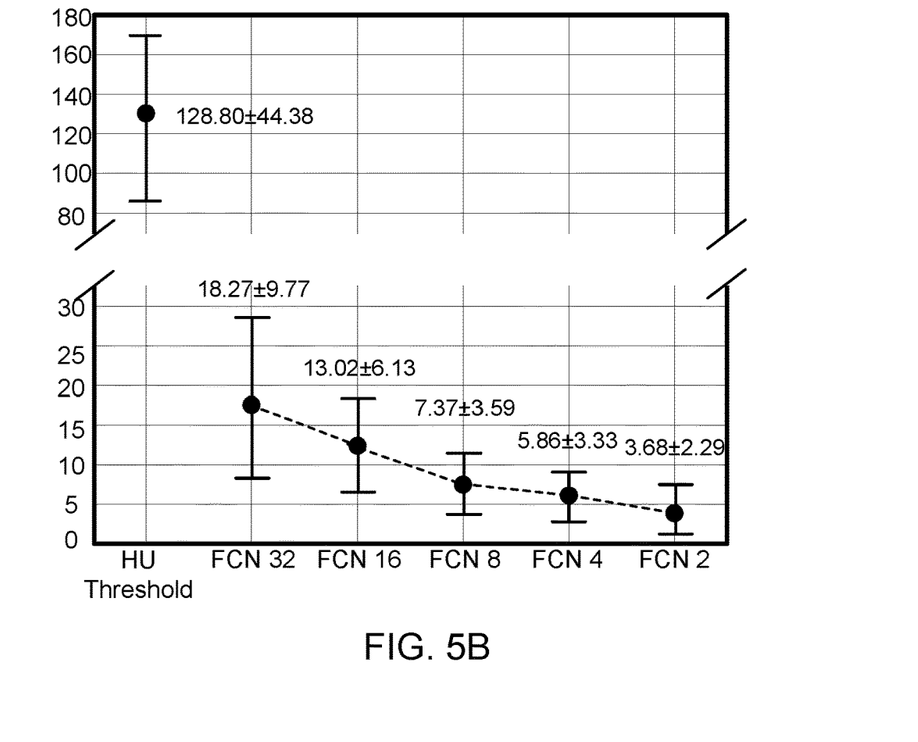
FIG. 5B is a graph of cross sectional area (CSA) error for the example with FIG. 5A.

Referring to FIGS. 5A and 5B, the five different FCN models were compared to the previously described HU thresholding method. All numbers are reported as mean±SD. Performance was evaluated using the Dice Similarity Coefficient (DSC) in FIG. 5A and muscle CSA error in FIG. 5B.

Even the most coarse-grained FCN model (FCN-32s) achieved 0.79±0.06 of DSC and 18.27±9.77% of CSA error, markedly better than the HU thresholding method without human tuning. Performance increased as the number of features of different layers were fused. The most fine-grained FCN model achieved DSC of 0.93 and CSA error of 3.68% on average, representing a 59% improvement in DSC and an 80% decrease in CSA error when compared to the most coarse-grained model.

Figure 6A:
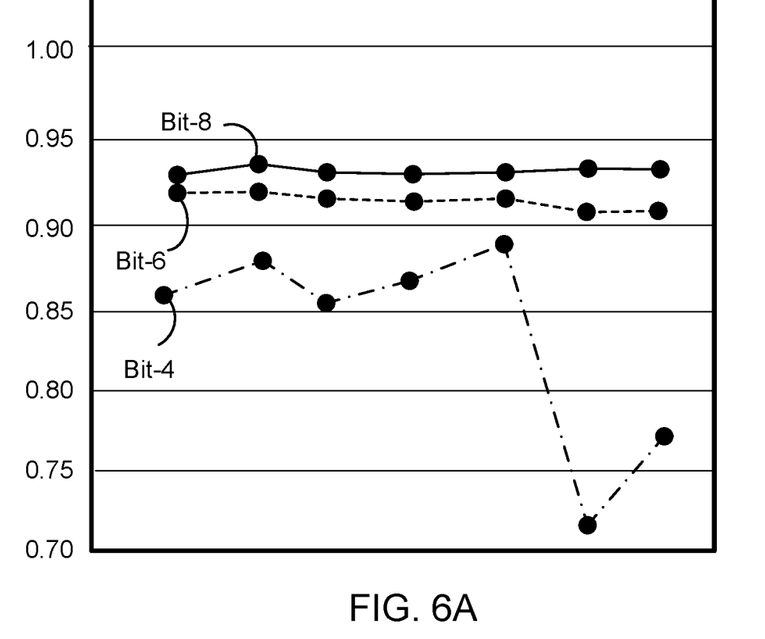
FIG. 6A is a graph of Dice Similarity Coefficient (DSC) from one example application of the present disclosure.
Figure 6B:
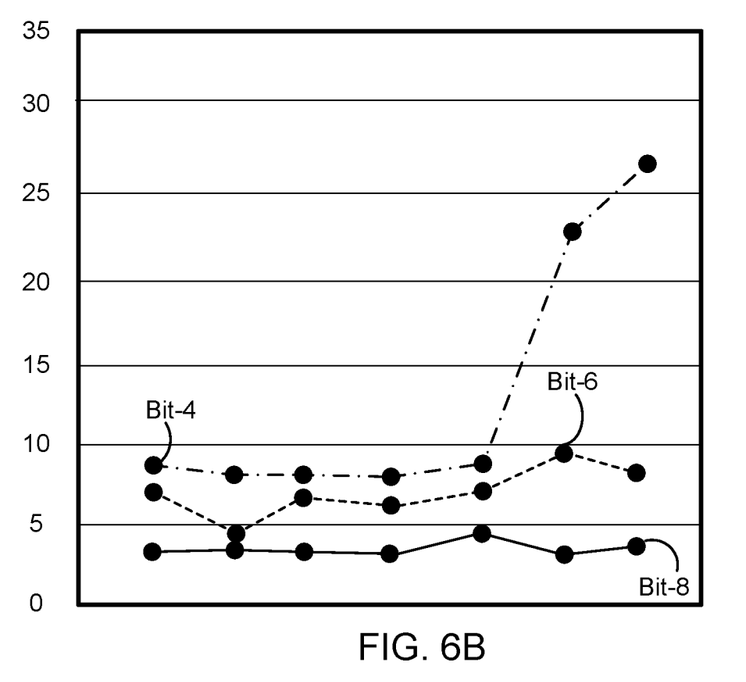
FIG. 6B is a graph of cross sectional area (CSA) error for the example with FIG. 6A.

Referring to FIGS. 6A and 6B, results of the systematic experiment comparing seven different combinations of window settings for each bit depth per pixel are presented. Performance of FCN-2s when input images are generated with different window settings (WL, WW) for each bit depth per pixel (BIT). The selected window settings were (40, 400), (−40,400), (100,400), (160,600), (40,240), (40,800), and (40,1200). DSC, shown in FIG. 6A, and CSA error, shown in FIG. 6B, were not meaningfully influenced by changes in window ranges as long as 256 gray levels per pixel (bit8) were available. When 6-bit depth per pixel was used, performance was similar compared to the results of 8-bit cases. However, model performance deteriorated when 8-bit pixels were compressed to 4-bit pixels.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a report of a risk stratification for a subject using medical imaging, the method comprising:
   a) acquiring an image of a region of interest of the subject;
   b) segmenting the image using a deep segmentation artificial intelligence network to generate a segmented image that distinguishes between at least two different materials in the image at a pixel-level;
   c) calculating a morphological age of the subject using the segmented image; and
   d) generating a report of risk stratification of the subject at least based upon the calculated morphological age; and
   measuring at least one of a Dice Similarity Coefficient (DSC) or a cross sectional area (CSA) error between a ground truth and a predicted segmentation of the image and selecting the artificial intelligence network from a plurality of networks based on a minimizing of the DSC or CSA.

2. The method of claim 1 wherein the artificial intelligence network is a fully convolutional neural network adapted to segment the image at a pixel-level.

3. The method of claim 1 wherein the artificial intelligence network is a fully convolutional neural network (FCN) and the plurality of networks include different layered FCNs including at least an FCN of 32 layers, an FCN of 16 layers, an FCN of 8 layers, an FCN of 4 layers, and an FCN of 2 layers.

4. The method of claim 1 wherein the image is a computed tomography (CT) image.

5. The method of claim 1 further comprising converting the image to a grayscale image by converting from Hounsfield Units (HU) of the image using a grayscale.

6. The method of claim 5 wherein the converting includes setting grayscale values below a selected window width to zero and setting grayscale values above a window width to a maximum ($2^{BIT}-1$), wherein BIT represents the available number of bits per pixel, and wherein grayscale values within the window width are determined using a slope ($2^{BIT}-1$/window width).

7. The method of claim 1 wherein calculating the morphological age of the subject includes quantifying a cross sectional area of the segmented image.

8. The method of claim 1 wherein generating the report of risk stratification of the subject includes determining at least one of a preoperative risk, a prediction of death, a tolerance to major surgery or chemotherapy, morbidity, mortality, or an expected length of hospital stay.

9. The method of claim 1 wherein the artificial intelligence network is trained with at least one labelled image.

10. The method of claim 1 wherein the segmenting is performed in real-time.

11. A system for generating a report of a risk stratification for a subject from medical images, the system comprising:
    a computer system configured to:
        i) acquire a medical image of a region of interest of the subject;
        ii) generate a segmented image by segmenting the image using a pixel-level deep artificial intelligence network to distinguish between at least two different materials in the image;
        iii) calculate a morphological age of the subject using the segmented image; and
        iv) generating a report of risk stratification of the subject based upon the calculated morphological age; and
    measuring at least one of a Dice Similarity Coefficient (DSC) or a cross sectional area (CSA) error between a ground truth and a predicted segmentation of the image and selecting the artificial intelligence network from a plurality of networks based on a minimizing of the DSC or CSA.

12. The system of claim 11 wherein the artificial intelligence network is a fully convolutional neural network adapted to segment the image at a pixel-level.

13. The system of claim 11 wherein the artificial intelligence network is a fully convolutional neural network (FCN) and the plurality of networks include different layered FCNs including at least an FCN of 32 layers, an FCN of 16 layers, an FCN of 8 layers, an FCN of 4 layers, and an FCN of 2 layers.

14. The system of claim 11 wherein the image is a computed tomography (CT) image.

15. The system of claim 11 further comprising converting the image to a grayscale image by converting from Hounsfield Units (HU) of the image using a grayscale.

16. The system of claim 15 wherein the converting includes setting grayscale values below a selected window width to zero and setting grayscale values above a window width to a maximum ($2^{BIT}-1$), wherein BIT represents the available number of bits per pixel, and wherein grayscale values within the window width are determined using a slope ($2^{BIT}-1$/window width).

17. The system of claim 11 wherein calculating the morphological age of the subject includes quantifying a cross sectional area of the segmented image.

18. The system of claim 11 wherein generating the report of risk stratification of the subject includes determining at least one of a preoperative risk, a prediction of death, a tolerance to major surgery or chemotherapy, morbidity, mortality, or an expected length of hospital stay.

19. The system of claim 11 wherein the artificial intelligence network is trained with at least one labelled image.

20. The system of claim 11 wherein the computer system is configured to perform the segmenting in real-time.

* * * * *